United States Patent
Ryan et al.

(10) Patent No.: US 6,342,615 B1
(45) Date of Patent: Jan. 29, 2002

(54) GLYCIDYL ESTER ADDUCTS HAVING INCREASED GLASS TRANSITION TEMPERATURES

(75) Inventors: Richard William Ryan, Kingwood, TX (US); Gerald G. McGlamery, Jr., Baton Rouge, LA (US); Ralph Martin Kowalik, Kingwood, TX (US); Michael J. Keenan, Baton Rouge, LA (US)

(73) Assignee: ExxonMobil Chemicals Patents Inc., Houston, TX (US)

( * ) Notice: Subject to any disclaimer, the term of this patent is extended or adjusted under 35 U.S.C. 154(b) by 0 days.

(21) Appl. No.: 09/566,314

(22) Filed: May 8, 2000

Related U.S. Application Data

(63) Continuation of application No. 08/967,634, filed on Nov. 10, 1997, now Pat. No. 6,136,991, which is a continuation-in-part of application No. 08/861,408, filed on May 21, 1997, now Pat. No. 5,880,297.
(60) Provisional application No. 60/018,073, filed on May 21, 1996.

(51) Int. Cl.[7] .................... C07D 301/32; C07D 303/16; C08F 24/00; C08F 124/00; C08F 224/00
(52) U.S. Cl. .................... 549/541; 549/557; 525/327.3; 526/273
(58) Field of Search ................... 549/541, 557; 525/327.3; 526/273

(56) References Cited

U.S. PATENT DOCUMENTS

| | | | |
|---|---|---|---|
| 3,075,999 A | 1/1963 | June et al. | 260/348.6 |
| 3,142,686 A | 7/1964 | Kreps et al. | 260/348 |
| 3,178,454 A | 4/1965 | Kloos et al. | 260/348.6 |
| 3,275,583 A | 9/1966 | Kloos | 260/22 |
| 3,397,176 A | 8/1968 | Drost | 260/47 |
| 3,878,029 A | 4/1975 | Baird et al. | 159/6 WH |
| 4,160,692 A | 7/1979 | Mitchell et al. | 159/6 W |
| 4,173,246 A | 11/1979 | Nunlist et al. | 159/6 W |
| 4,276,212 A | 6/1981 | Khanna et al. | 260/39 |
| 5,880,297 A | 3/1999 | Ryan et al. | 549/541 |

FOREIGN PATENT DOCUMENTS

| JP | 46037 326 B | 11/1971 |
|---|---|---|

OTHER PUBLICATIONS

Mutzenberg, A.B., et al, "Agitated Thin–Film Evaporators: A Three Part Report," Parts 1 to 3, Chemical Engineering, Sep. 13, 1965.

Kaufman, H.S., et al., Introduction to Polymer Science & Technology: An SPE Textbook, editors: John Wiley & Sons, 1977.

Brandup, J., et al, Polymer Handbook, editors: John Wiley & Sons, 1989.

Fox, T.G., et al, Am. Phys. Soc., 1:123 (1956).

*Primary Examiner*—Ba K. Trinh
(74) *Attorney, Agent, or Firm*—Douglas J. Collins

(57) ABSTRACT

The invention provides for a purified glycidyl ester product prepared from neo acids wherein said ester product is recovered as a light fraction from a glycidyl ester reaction product composition that has been subjected to conditions of temperature and vacuum in a thin film, short pass distillation evaporator, said purified glycidyl ester product further characterized that its polymerizable reaction product with methacrylic acid has a higher effective glass transition temperature as compared with the polymerizable reaction product with methacrylic acid of said glycidyl ester reaction product composition prior to purification.

7 Claims, No Drawings

GLYCIDYL ESTER ADDUCTS HAVING INCREASED GLASS TRANSITION TEMPERATURES

This application is a continuation of US Application Ser. No. 08/967,634, filed Nov. 10, 1997, which is in turn continuation-in-part of U.S. application Ser. No. 08/861, 408, filed May 21, 1997, now U.S. Pat. No. 5,880,297 which is in turn based on Provisional Application 60/018,073, filed May 21, 1996.

BACKGROUND OF THE INVENTION

This invention relates to glycidyl esters whose adducts with acrylic or methacrylic acid exhibit increased effective glass transition temperatures and their use as reactants in preparing polymer compositions.

1. Description of Related Art

Glycidyl esters of monocarboxylic acids are well known materials which are useful as chemical intermediates in the preparation of acrylic, polyester, and alkyd resins, or as reactive diluents in the preparation of thermoset epoxy, polyester and urethane paints and coatings.

Of particular interest are glycidyl esters of aliphatic monocarboxylic acids represented by the empirical formula

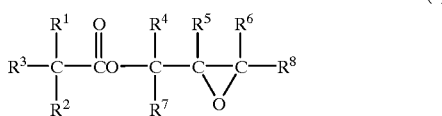

(1)

wherein $R^1$, $R^2$ and $R^3$ each represent the same or different alkyl radicals of normal or branched structure containing 1–20 carbon atoms, and $R^4$ through $R^8$ each represent hydrogen or a hydrocarbyl group containing 1–3 carbon atoms. A more preferred product is one where $R^1$ through $R^3$ are alkyl radicals containing a sum total of 3–20 carbon atoms and where $R^4$ through $R^8$ are each hydrogen, e.g., the reaction product of neodecanoic acid ($R^1+R^2+R^3=C_8$) and epichlorohydrin.

Glycidyl esters of this general type and their method of preparation are disclosed in U.S. Pat. No. 3075999, U.S. Pat. No. 3178454, U.S. Pat. No. 3275583 and U.S. Pat. No. 3397176, the complete disclosures of each of which are incorporated herein by reference.

Such glycidyl esters can be made by reacting an alkali salt of the carboxylic acid with a halo-substituted monoepoxide such as an epihalohydrin, e.g., epichlorohydrin (1–20 molar excess). The mixture is heated (50°–150° C.) in the presence of a catalyst forming glycidyl ester plus alkali salt and water. The water and excess epihalohydrin are removed by azeotropic distillation, and the salt by-product, e.g., NaCl, is removed by filtration and/or washing. The glycidyl esters can also be made by reacting the carboxylic acid directly with epichlorohydrin under similar process conditions. The chlorohydrin ester intermediate formed during this reaction is subsequently treated with an alkaline material, e.g., sodium or potassium hydroxide, which yields the desired glycidyl ester. By-product salt is removed by washing and/or filtration, and water is removed by drying.

Investigations of these reactions reveal that several heavier by-products are produced during the reactions to varying degrees, and species which add color to the main product are contained within the heavier by-products. The heavier by-products include the reaction products of the glycidyl ester product and/or the chlorohydrin ester intermediate with either unreacted epichlorohydrin, unreacted monocarboxylic acid or salt and/or water at various stages of the synthesis process in accordance with the following overall reaction schemes:

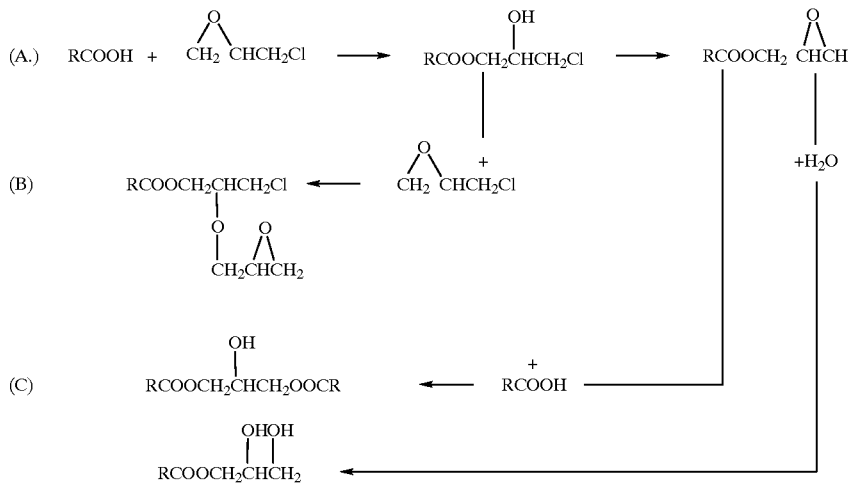

The heavier by-products may also include further reaction products of compounds A, B and/or C with the glycidyl ester product and other species present. Generally speaking, one or a combination of these or other unidentified heavies are present in the glycidyl ester reaction product at levels in excess of about 3 wt %, e.g., about 4–12 wt %.

Because glycidyl esters are thermally and chemically reactive molecules, separation of these by-products from glycidyl esters is not easily accomplished. Standard atmospheric distillation techniques have been found to increase the amount of by-products as well as the degree of color of the esters. It is believed that this increase in color is caused by the reaction at elevated temperatures, as encountered during distillation, of the glycidyl functionality present in the desired product with functionalities present in the by-products, thereby forming additional by-products. Surprisingly, standard vacuum distillation has also been found to be ineffective in reducing the initial or aged color of the glycidyl esters, and tends to worsen the color problem.

Japanese Patent 46 (1971) 37326 discloses a process for manufacturing an unsaturated organic acid glycidyl ester by reacting a salt of the unsaturated acid (acrylic or methacrylic acid) with a molar excess of epichlorohydrin. The residual unreacted epichlorohydrin is then distilled out of the reaction product using thin film distillation techniques. The resulting product is further distilled using thin film evaporation techniques to provide a purer product having improved color stability after periods of storage. The reference teaches that the process avoids the polymerization of the acrylic monomers observed during conventional distillation and thereby eliminates the need to include a polymerization inhibitor in the reaction product which inhibitor retards polymerization of the unsaturated monomers but which also reacts with the epoxy compounds to give products of less purity.

Copending U.S. application Ser. No. 08/861,408, filed May 21, 1997, discloses a process for the distillation of the glycidyl ester reaction product composition of one or more straight or branched chain saturated monocarboxylic acids or salts thereof and a halo-substituted monoepoxide comprising subjecting said reaction product composition to conditions of temperature and vacuum in a thin film, short pass distillation apparatus, and recovering a light fraction having a Pt—Co color value of less than about 100 after 20 days storage in contact with air at about 125° C., as measured in Pt—Co units in accordance with ASTM D1209.

Products produced according to that invention are of significantly reduced initial color and exhibit improved color stability after periods of storage, thereby minimizing any color contribution by these products in systems where they are used, e.g., in the preparation of alkyd, polyester or acrylic resins and especially in coating and paint formulations containing these products.

Various researchers have been pursuing new polymer compositions which will give a better balance of properties when these polymeric binders are formulated into paints. Of particular importance is maintaining good film properties (hardness, flexibility, durability, etc.) as polymer molecular weights and viscosity are reduced. The latter is essential to reduce the amount of solvent, i.e., volatile organic compounds (VOCs), in the paints. These VOCs are being regulated to reduce air pollution.

One important factor which influences paint and film properties is the glass transition temperature (Tg) of the polymer(s) and/or oligomer(s) used as paint binders. Usually a specific value or range of Tg is required to meet the performance requirements of a given application. Another important factor which influences paint and film properties is the nature of the functional group incorporated in the polymer. In many cases this is a hydroxyl group. One of the better hydroxyl groups used in acrylic polymers, for example, comes from an adduct of glycidyl neodecanoate and either methacrylic acid or acrylic acid. These adducts can impart improved paint and film properties over similar acrylic polymers (same OH concentration, Tg, and molecular weight) made with other hydroxy functional monomers. Improved weatherability and chemical resistances and lower viscosity (i.e., lower VOC) are notable features attributable to these adducts.

It is a significant challenge, however, to obtain useful lower molecular weight acrylic polymers with hydroxy (OH) functionalities based solely on these adducts. In particular, as molecular weights decrease, one must increase the relative proportion of hydroxy functional monomers to maintain good film properties. With glycidyl neodecanoate adducts which have relatively low effective Tgs, this can lower the maximum polymer Tg below desired levels. Consequently, to get the best possible film properties one would like to have a monomer which provides the durability and chemical resistance of the glycidyl neodecanoate adducts, but with a higher Tg.

We have discovered that by using purified glycidyl esters of neo acids particularly those derived from isobutylene and/or isobutylene oligomers, one can obtain glycidyl ester adducts with high effective Tgs. Such glycidyl neopentanoate, glycidyl neononanoate, etc., adducts offer the possibility to make improved resin binders with desired Tgs, lower molecular weights (lower VOC) and superior film properties.

SUMMARY OF THE INVENTION

The present invention provides a glycidyl ester product having the formula:

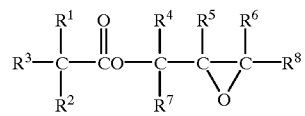

wherein $R^1$, $R^2$ and $R^3$ each represent the same or different alkyl radicals of normal or branched structure containing 1–20 carbon atoms and $R^4$ through $R^8$ each represent hydrogen or a hydrocarbyl group containing 1–3 carbon atoms, and wherein said ester product is recovered as a light fraction from a glycidyl ester reaction product composition that has been subjected to conditions of temperature and vacuum in a thin film, short pass distillation evaporator, said purified glycidyl ester product further characterized that its polymerizable reaction product with methacrylic acid has a higher effective glass transition temperature as compared with the polymerizable reaction product with methacrylic acid of said glycidyl ester reaction product composition prior to purification.

The invention also provides for coating and paint formulations containing the purified glycidyl ester product as a reactive diluent or as a component useful in the preparation of resinous binder materials such as alkyd, polyester or acrylic resins.

DETAILED DESCRIPTION OF THE INVENTION

Glycidyl ester products which are distilled in accordance with this invention are of the general structure set forth in formula 1 in the Background section of this disclosure, and which are the reaction product of one or a mixture of saturated monocarboxylic acids, preferably the alkali or tertiary ammonium salts thereof, and a halo-substituted monoepoxide.

Suitable saturated monocarboxylic acids which may be used to prepare the glycidyl esters are tertiary alkyl acids wherein $R^1$, $R^2$, and $R^3$ in formula 1 above each contain 1–20 carbon atoms, more preferably 1–12 carbon atoms. More preferably, the sum total of $R^1$, $R^2$ and $R^3$ is 3 to 15 carbon atoms and most preferably about 8 carbon atoms.

Suitable such acids include neopentanoic (pivalic), neodecanoic, neotridecanoic and neononanoic acids. A particularly preferred acid is a neodecanoic acid prepared by the reaction of mono olefins averaging 8–10 carbon atoms in the molecule with carbon monoxide and water in the presence of a suitable acidic catalyst.

The most preferred saturated monocarboxylic acids are those where the segment:

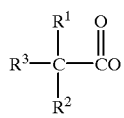

has a neo section of isobutyl or an isobutyl oligomer such as diisobutyl.

Suitable halo-substituted monoepoxides which may be used to prepare the glycidyl esters include epichlorohydrin, 1-chloro-2,3-epoxyhexane, 1-chloro-2,3-epoxy-4-butyloctane, 1-chloro-2,3-epoxy heptane, 3-chloro-4,5-epoxydodecane, 3-chloro-4,5epoxynonane, 1-chloro-2,3-epoxy-4-cyclohexyloctane and like materials.

Glycidyl esters of this type and their method of synthesis are well known in the art and are particularly described in the aforementioned U.S. Pat. No. 3178454 and U.S. Pat. No. 3075999. Isobutylene and diisobutylene are suitable starting monomers to prepare neo acids suitable for synthesis of the glycidyl esters of the invention.

A thin film, short pass distillation evaporator is used to separate the main glycidyl ester reaction product from by-products of the A, B and/or C type as described in the Background section of this disclosure, as well as other "heavies" which may be present as impurities in the glycidyl ester reaction product. The term "heavies" as used herein means compounds or mixtures of compounds having a molecular weight higher than the target glycidyl esters. The use of such evaporators allows for rapid vacuum stripping of the glycidyl ester from the mixed reaction product without subjecting the product to excessively high temperatures or for periods of time sufficient to cause thermal degradation of the product and the further development of one or more of the heavier by-products which tend to cause coloration of the product. Typical such evaporators include shell and tube evaporators, falling or rising film evaporators and wiped film evaporators. A preferred evaporator for use in preparing the purified products of the present invention is a wiped film evaporator.

The wiped film evaporators (also referred to as agitated thin-film evaporators) preferred for use in the distillation process are known in the art and are available commercially. A general discussion of the principle of operation of these evaporators may be found in the publication: "Agitated Thin-Film Evaporators: A Three Part Report", Parts 1 to 3; A. B. Mutzenburg, N. Parker and R. Fischer; Chemical Engineering, Sep. 13, 1965.

Typically, wiped film evaporators comprise a cylindrical evaporating vessel. The vessel may be either vertical or horizontal, with vertically arranged vessels being preferred. The evaporator further comprises a rotor mounted within the cylindrical evaporating vessel and provided with a number of wiper blades or wiper rollers, and a motor is provided to drive the rotor. The rotor is arranged within the cylindrical evaporating vessel so that, upon rotation by the motor, the wipers are caused to move over the inner surface of the cylindrical vessel. The wipers may contact the inner surface of the cylindrical vessel or, alternatively, a small gap or clearance may be left between the tips of the wiper blades or the tangential line of the wiper rollers and the inner surface of the cylindrical vessel.

In operation, the mixture to be separated is fed, supplied or subjected to the evaporator and forms a thin film over the inner surface of the cylindrical vessel. The film is heated, typically by means of indirect heat exchange with a heating medium through the wall of the cylindrical vessel, such as steam or hot oil. The action of the wiper blades in passing over the surface is to agitate the film of the glycidyl ester composition which forms on the inner cylinder surface, resulting in turbulence in the film, which in turn improves heat and mass transfer. In addition, the wiper blades or wiper rollers insure an even distribution of the composition over the inner surface of the vessel and prevent channeling of the liquid as it passes across the surface. Under the action of the wiper blades or wiper rollers and the heating, the lighter components of the mixture are caused to evaporate.

The light product is removed from the evaporator as a vapor and is subsequently condensed. Condensing is conveniently effected by indirect heat exchange with a cooling medium such as water. The condenser may be separate from the evaporator vessel or may be located within the vessel. In the latter case, the vessel will comprise a first evaporating section in which the rotor and wiper blades are arranged and a second condensing section in which the condenser is housed. If desired, a separating section may be disposed between the evaporating section and the condensing section to allow removal of any liquid droplets entrained in the vapor prior to condensing.

The heavy product is removed from the evaporator as a liquid flowing from the inner surface of the cylindrical vessel. The wiped film evaporator is operated under a vacuum. Suitable pumps for the generation and maintenance of the vacuum are well known in the art. Typical examples of suitable pumps include steam ejector pumps and diffusion vacuum pumps.

According to the process, the mixture to be separated is first heated to a temperature sufficient to reduce the viscosity of the mixture, thereby allowing it to more readily flow. The mixture is then introduced into the evaporator to form a thin film on the inner surface of the heat exchanger surface of the evaporator vessel, e.g., a cylindrical drum or a series of tubes. The operating pressures for the thin film evaporator will vary according to the precise nature of the ester feedstock. Typical operating pressures are in the range of about 0.05 to about 50 mm Hg, more preferably from about 0.5 to about 10 mm Hg. Typical operating temperatures in the evaporator will be in the range of from about 50° C. to about 200° C., more preferably from about 60° C. to 175° C. The average residence time of the glycidyl ester reaction product composition in the evaporator is relatively low as compared with that of a conventional batch distillation apparatus, and this is believed to be a key factor in the avoidance of discoloration of the distillate. Typical average residence time is in the range of from about 0.2 to about 10 minutes, more preferably less than about 2 minutes, depending upon the nature of the feedstock and the design of evaporator being employed. It is important, however, that the operating temperature is not so high as to lead to a substantial degree of thermal degradation of the mixture being processed at the particular residence time and that the operating conditions of temperature and pressure are selected to ensure that such high temperatures are not required.

Suitable wiped film evaporators which may be used in accordance with this invention include apparati of the type disclosed in U.S. Pat. No. 3878029, U.S. Pat. No. 4160692 or U.S. Pat. No. 4173246.

Preferred glycidyl esters purified in accordance with this invention will generally exhibit boiling points in the range of from about 60 to 90° C. at 3mm Hg and a content of by-products such as A, B and/or C described in the Background section of this disclosure of less than 4 wt %, more preferably less than 2 wt % and most preferably less than 0.5 wt %. Coloration of the distilled product is in many cases reduced at least 50%, more preferably at least 60%, compared with the product coloration prior to distillation, as measured using the Pt—Co scale in accordance with ASTM test method D 1209. Glycidyl esters purified in accordance with this invention generally exhibit initial Pt—Co color values of less than 40 units prior to heat storage, more preferably in the range of 5–30 Pt—Co units, and values of less than about 100 Pt—Co units after 20 days storage in air at about 125° C., or values of less than about 50 Pt—Co units after 20 days storage under an inert gas such as nitrogen at about 125° C. These products also exhibit an at least about 3% reduction in epoxy equivalent weight (EEW) as compared with the non-purified starting material, more preferably a 4 to 8% reduction in EEW.

It has also been found that the purified glycidyl esters produced in accordance with this invention provide polymer compositions with a higher glass transition temperature (Tg) when used as a reactive diluent or monomer in the preparation of the polymer composition. For example, the polymerizable reaction product (ester) of the purified glycidyl ester with acrylic or methacrylic acid (which forms a hydroxy functional (meth)acrylate monomer) exhibits a higher effective Tg than the corresponding reaction product made using the non-purified glycidyl ester or an ester purified by other processes such as atmospheric distillation. Reaction products of preferred glycidyl ester materials with methacrylic acid will exhibit an effective Tg in the range of about 20° C. to 90° C., more preferably from about 20° C. to 50° C.

The glass transition temperature is related to the softening point of material and can be measured via a variety of techniques as discussed in *Introduction to Polymer Science and Technology: An SPE Textbook*, by H. S. Kaufman and J. Falcetta, John Wiley & Sons, 1977, and *Polymer Handbook* by J. Brandup and E. H. Immergut, editors, John Wiley & Sons, 1989. Tg values for high molecular weight homopolymers of various monomers are also available in these references. Values for copolymers can be calculated via the Fox Equation (Fox T. G., Bull Am. Phys. Soc. 1:123 (1956), i.e.

$$\frac{1}{TG} = \sum \frac{W_i}{Tg_i},$$

where Wi is the weight fraction of the i th monomer in the copolymer, $T_{g,i}$ is the glass transition temperature for a high molecular weight homopolymer of the i th monomer; and all temperatures are expressed in absolute units. Alternatively, if Tgs are known for all but one of the monomers and weight fractions are known for all monomers, a measurement of the Tg of the copolymer provides sufficient information to calculate an effective Tg for the last monomer. The latter procedure is used to calculate effective Tgs for the various glycidyl ester-methacrylic acid adducts used as monomers in Examples 8–12 of this application.

Since the number average molecular weights of the copolymers synthesized in Examples 8–12 (about 2000) is somewhat lower than values typically used with the Fox equation (more than about 10,000), the calculated Tg values for the adducts may be lower than their expected values. In particular, Tg values for high molecular weight polymers are generally independent of specific molecular weight, but Tg values for lower molecular weight polymers (less than about 10,000) often decrease as molecular weights decrease.

The purified glycidyl esters may be used in the preparation of acrylic resins which contain at least one hydroxy functional alkyl (meth) acrylate. This monomer will form by the reaction, under polymerization conditions, of the purified glycidyl ester and acrylic or methacrylic acid. In general, acrylic polymer resins may be prepared from at least one hydroxy functional alkyl (meth)acrylate, including the adduct described above, and at least one non-hydroxy substituted alkyl (meth)acrylate. Additional hydroxy-substituted alkyl (meth) acrylates which can be employed as monomers comprise members selected from the group consisting of the following esters of acrylic or methacrylic acid and aliphatic glycols: 2-hydroxyethyl acrylate, 3-chloro-2-hydroxypropyl acrylate, 1-hydroxy- 2-acryloxy propane; 2-hydroxybutyl acrylate; 4-hydroxybutyl acrylate; diethyleneglycol acrylate; 5-hydroxypentyl acrylate; 6-hydroxyhexyl acrylate; triethyleneglycol acrylate; 7-hydroxyheptyl acrylate; 1-hydroxy-2-methacryloxy propane; 2-hydroxypropyl meth-acryloxy propane; 2-hydroxypropyl methacrylate; 2,3-dihydroxypropyl meth-acrylate; 2-hydroxybutyl methacrylate; 3-hydroxybutyl methacrylate; 2-hydroxyethyl methacrylate; 4-hydroxy butylmethacrylate; 3,4-dihydroxybutyl meth-acrylate; 5-hydroxypentyl methacrylate; and 7-hydroxyheptyl methacrylate. Although one of ordinary skill in the art will recognize that many different hydroxy-substituted alkyl (meth)acrylates including those listed above could be employed, the preferred hydroxy functional monomers for use in the resins are hydroxy substituted alkyl (meth) acrylates having a total of 5 to 7 carbon atoms, i.e. esters of $C_2$ to $C_3$ dihydric alcohols and acrylic or methacrylic acids. Illustrative of particularly suitable hydroxy-substituted alkyl (meth) acrylate monomers are 2-hydroxyethyl methacrylate, 2-hydroxyethyl acrylate, 2-hydroxybutyl acrylate, 2-hydroxypropyl methacrylate, and 2-hydroxypropyl acrylate.

Among the non-hydroxy substituted alkyl (meth)acrylate monomers which may be employed are alkyl (meth) acrylates (as before, meaning esters of either acrylic or methacrylic acids). Preferred nonhydroxy unsaturated monomers are esters of $C_1$, to $C_{12}$ monohydric alcohols and acrylic or methacrylic acids, e.g., methyl methacrylate, hexyl acrylate, 2-ethylhexyl acrylate, lauryl methacrylate and the like. Examples of particularly suitable monomers are butyl acrylate, butyl methacrylate and methyl methacrylate.

Additionally, the acrylic copolymer resin may include in their composition other monomers such as acrylic acid and methacrylic acid, monovinyl aromatic hydrocarbons containing from 8 to 12 carbon atoms (including styrene, alpha-methyl styrene, vinyl toluene, t-butyl styrene, chlorostyrene and the like), vinyl chloride, vinylidene chloride, acrylonitrile, and methacrylonitrile.

The acrylic copolymer preferably has a number average molecular weight between about 1000 and 6000, more preferably between about 1500 and 5000. Preferred acrylic polymers will contain at least about 5wt % of the purified glycidyl ester component, preferably about 5–35wt %, based on resin solids.

Acrylic polymers of this type and curable coating or paint formulations prepared therefrom containing an amino crosslinker are disclosed in U.S. Pat. No. 4276212. These polymers are generally polymerized in organic solvent solution using free radical catalysts such as organic peroxides or azobis-isobutyronitrile.

Alkyd resins may be prepared by reacting the purified glycidyl ester with polybasic carboxylic acids or anhydrides thereof Illustrative examples of polybasic carboxylic acids include: terephthalic acid, malonic acid, succinic acid, glutaric acid, adipic acid, azeleic acid, sebacic acid, maleic acid, fumaric acid, phthalic acid, tetrahydrophthalic acid, isophthalic acid and dimerized fatty acid of drying oils such as soybean oil. Examples of suitable dicarboxylic acid anhydrides are those of succinc acid, glutaric acid, maleic acid, phthalic acid, tetrahydrophthalic acid and hexahydrophthalic acid as well as Diels-Alder adducts of maleic anhydride with various dienes such as terpenes and cyclopentadiene.

Preferred alkyd resins include those disclosed in U.S. Pat. No. 3275583 and U.S. Pat. No. 3397176.

The purified glycidyl esters may also be used as a reactive diluent in resin systems where the epoxy functionality is caused to react with some functionality present on the resin binder. Such resin systems include polyester resins, polycarbonate resins, epoxy resins and like resins, as well as acrylic and alkyd resins.

The following examples are illustrative of the invention.

EXAMPLE 1

A commercially available glycidyl ester of neodecanoic acid and epichlorohydrin marketed by Exxon Chemical Corporation under the tradename GLYDEXX® ND-101 was provided. This material has an atmospheric boiling point in the range of about 250° C. to 280° C. and a content of by-products "heavies" of about 10 wt %. Five hundred grams of the starting glycidyl ester was fed through a Pope Scientific Model 40450 two inch molecular still (cylinder) equipped with carbon wiper blades. The still temperature was maintained at 115° C. and the pressure was 3 mm Hg. Flow rate of the ester was maintained at 80–100 g/hr. The overhead distillate was condensed and collected, yielding a total of 466.1 grams of overhead and 30.7 grams of non-distilled bottoms. The distillate and starting material were analyzed by gas chromatography using a Hewlett Packard 5890 instrument equipped with a 1 micrometer DB-1 column. Analysis of the distillate showed about a 50% reduction of the heavier ends (heavies) as compared with the glycidyl ester prior to distillation as shown in Table 1 and a reduction of the epoxy equivalent weight (EEW) from 254 to 241. The latter was measured in accordance with a modification of ASTM method D1652B.

TABLE 1

Gas Chromatography Analytical Results

| Peak Assignment | Retention Times (minutes) | Starting Material (area %) | Distillate (area %) |
|---|---|---|---|
| Lights | 5.4–34.7 | 2.04 | 2.01 |
| Glycidyl Ester-Product (1) | 34.7–44.0 | 88.29 | 93.34 |
| Heavies (2) | 44.0–56.3 | 9.67 | 4.65 |

(1)Includes glycidyl neononanoate, glycidyl neodecanoate, glycidyl undecanoate, Compound C and chlorohydrin ester intermediates peaks
(2)Includes Compounds A and B peaks.

One of the particular advantages afforded by the purification process of this invention is a reduction in the EEW of the purified glycidyl ester product as compared with the starting product. For example, the product of Example 1 shows about a 5% EEW reduction (from 254 to 241) which is indicative of a more highly purified product. The theoretically pure product would have an EEW of about 228. A lower EEW means a higher epoxy concentration in the product which leads to greater efficiency when these glycidyl esters are used as resin modifiers or reactive diluents in other polymer systems.

EXAMPLE 2

Color comparisons of the pre-distilled and post distilled glycidyl ester composition were performed in accordance with ASTM-D1209. Also, the resistance to further discoloration of the glycidyl esters was evaluated in a heat stability test. For this test, approximately 125 ml samples of glycidyl esters were placed in 8 ounce jars. The jars were covered with foil-lined phenolic caps which were further secured with electrical tape. The sealed jars were about one-half full of glycidyl ester and one-half full of air. They were placed into a 125° C. oven which was continuously purged with nitrogen. After a few days, the jars were removed from the oven and allowed to cool about 1 to 2 hours. Colors of the samples were then measured via procedures described in ASTM D1209. This procedure was repeated with the heat aged samples up to a total heating period of 20 days. Results of color comparisons between the non-distilled product and the product distilled in accordance with Example 1 are shown in Table 2.

TABLE 2

| DAYS HEATED | NON-DISTILLED | EXAMPLE 1 color (Pt-Co Scale) |
|---|---|---|
| Initial Samples | 50 | 10–15 |
| 2 | 50–60 | 15 |
| 4 | 50 | 15–20 |
| 6 | 50–60 | 15–20 |
| 8 | 45–50 | 20 |
| 10 | 45–50 | 20 |
| 20 | >250 | 80–90 |

The results in Table 2 show that the initial color of the GLYDEXX® product (50 Pt—Co units) was reduced to 10–15 Pt—Co units after the product was distilled in accordance with Example 1. The distilled product also demonstrated remarkable color stability after aging in air up to 20 days as compared with the starting product.

EXAMPLES 3–7

A set of glycidyl esters of commercial $C_5$, $C_9$, and $C_{10}$ neo acids were prepared by reacting the neo acids with epichlorohydrin as described above in this application. The neo acids are marketed by Exxon Chemical Company as Neo Pentanoic Acid, Neo 900 (neo nonanoic acid), and Neo Decanoic Acid (prime grade). The Neo Pentanoic Acid is made from isobutylene. The Neo 900 is made from octene as isobutylene dimers. The Neo Decanoic Acid is made from nonene as predominantly propylene trimers. The unpurified glycidyl ester of Neo Decanoic acid was a sample of the commercial product GLYDEXX® N-10 also marketed by Exxon Chemical Company. The unpurified glycidyl esters of Neo Pentanoic Acid and Neo 900 were prepared in laboratory scale apparatus.

A portion of each of these glycidyl esters was also purified in the Pope Scientific molecular still described in Example 1. Still temperatures were adjusted to accommodate the differing volatility's of the three esters and were approximately 65, 110 and 115° C. for the C5, C9 and C10 glycidyl esters, respectively. Pressures and flow rates were similar to those in Example 1. The esters were analyzed using the gas chromatograph and epoxy equivalent weight methods described in Example 1. Results are summarized in Table 3.

TABLE 3

Analyses of Glycidyl Esters of Neo Acids

| Example | 3 | 4 | 5 | 6 | 7 |
|---|---|---|---|---|---|
| Neo Acid | C5 | C9 | C9 | C10 | C10 |
| Purified | yes | no | yes | no | yes |
| Lights including C5 Glycidyl Ester (wt %) | 97.9 | 1.2 | 1.3 | 0.4 | 0.4 |
| C-9-C10 Glycidyl Ester Products (wt %) | 1.3 | 91.5 | 98.4 | 94.1 | 99.1 |
| Heavies (wt %) | 0.8 | 7.3 | 0.3 | 5.5 | 0.5 |
| Epoxy Equiv. Weight | 164 | 234 | 220 | 251 | 237 |

EXAMPLES 8–12

A set of acrylic resins were made with the glycidyl esters of examples 3–7 with the following basic compositions:

140 g xylene 59.5 g hydroxyethyl acrylate 51.0 g styrene 3.4 g methyl methacrylate 2.7 g n-butyl acrylate 51.0 g n-butyl methacrylate 42.8 g methacrylic acid 20.4 g tertiary butyl peroxybenzoate (initiator) plus 95% of the stoichiometric amount of the glycidyl ester required to react with the methacrylic acid based on the measured epoxy equivalent weights of the glycidyl esters. The ingredients were combined and reacted according to the following procedure:

Into a four-necked 1 liter round bottom flask equipped with heating mantle, reflux condenser, stirrer, thermocouple, and monomer/nitrogen injection port is placed 140 g of xylene. The flask is sealed and continuously purged with nitrogen. The contents are continuously stirred at a moderate rate and are heated to reflux. In a separate container the monomers and initiator are mixed.

After the xylene in the flask begins refluxing, the monomer/initiator mixture is injected into the flask and reflux in continued for 1 hour. The flask is then allowed to cool and contents are poured out into a storage jar. The Tg of the acrylic polymer is later measured by differential scanning calorimetry. An effective Tg of the glycidyl ester/methacrylic acid adduct is then calculated via the Fox equation and the known effective Tgs and weight fractions of the other monomers. Results for the 5 acrylic polymers are summarized in Table 4.

TABLE 4

Properties of Acrylic Polymers Containing Glycidyl Esters of Neo Acids

| Example | 8 | 9 | 10 | 11 | 12 |
|---|---|---|---|---|---|
| Glycidyl Ester from Example | 3 | 4 | 5 | 6 | 7 |
| Amount of Glycidyl Ester in polymer (g) | 78.4 | 111.1 | 104.5 | 117.3 | 112.6 |
| Mn of polymer | 2320 | 1550 | 2460 | 2210 | 2180 |
| Tg of polymer (° C.) | 24.2 | 12.7 | 22.8 | 5.3 | 8.2 |
| Effective Tg of glycidyl ester/methacrylic acid adduct (° C.) | 24.3 | 0.8 | 21.1 | −12.1 | −7.4 |

These data demonstrate that the adducts made with purified glycidyl neopentanoate and purified glycidyl neononanoate have the highest Tgs. They also demonstrate that purification via thin film evaporation raises the effective Tgs of both C9 and C10 glycidyl esters.

Coating/paint compositions can be prepared by combining any of the above resins with an amino crosslinker such as Resimene® 755 from Monsanto, a sulfonic acid catalyst such as Cycat® 600 from Cytec Industries, a flow and leveling agent such as BYK® 358 from BYK Chemie, an ultra-violet (UV) screen such as Tinuvin® 900 from Ciba-Geigy, a light stabilizer such as Tinuvin 123 also from Ciba-Geigy, amino propyl propanol or another catalyst inhibitor, and optionally solvent. A coating/paint layer may be produced by applying the composition to a substrate and heating to cure the coating e.g., 20 minutes at 121° C.

The purified glycidyl esters of this invention and their adducts with acrylic or methacrylic acid can be used as a monomer or reactive diluent in a composition intended for applications including: coatings, adhesives, sealants, caulks, concrete additives, non-wovens, construction products, building products, and the like. Coatings include automotive, decorative, wood, architectural, metal, coil, general industrial, and the like.

We claim:

1. A product comprising a coating wherein said coating comprises a purified glycidyl ester having a Pt—Co color value of less than about 100 after 20 days storage in contact with air at about 125° C. as measured in Pt—Co units in accordance with ASTM D1209 and containing less than about 4 wt % of molecular species heavier than said purified glycidyl ester.

2. The product of claim 1 wherein said coating is a paint.

3. The product of claim 1 wherein said purified glycidyl ester has the formula:

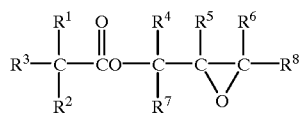

wherein $R^1$, $R^2$ and $R^3$ each represent the same or different alkyl radicals of normal or branched structure containing 1–20 carbon atoms and $R^4$ through $R^8$ each represent hydrogen or a hydrocarbyl group containing 1–3 carbon atoms.

4. The product of claim 3 wherein $R^1$, $R^2$ and $R^3$ are alkyl radicals containing a total of 3–15 carbon atoms and $R^4$ through $R^8$ are each hydrogen.

5. The product of claim 4 wherein $R^1$, $R^2$ and R3 contain a total of about 8 carbon atoms.

6. The product of claim 1 wherein said purified glycidyl ester contains less than 2 wt % of molecular species heavier than said purified glycidyl ester.

7. The product of claim 6 wherein said purified glycidyl ester contains less than 0.05 wt % of molecular species heavier than said purified glycidyl ester product.

* * * * *